US012304950B2

(12) United States Patent
Zang (10) Patent No.: US 12,304,950 B2
(45) Date of Patent: May 20, 2025

(54) METHODS OF PRODUCING USTEKINUMAB

(71) Applicant: Momenta Pharmaceuticals, Inc., Titusville, NJ (US)

(72) Inventor: Ru Zang, Auburndale, MA (US)

(73) Assignee: MOMENTA PHARMACEUTICALS, INC., Titusville, NJ (US)

(*) Notice: Subject to any disclaimer, the term of this patent is extended or adjusted under 35 U.S.C. 154(b) by 996 days.

(21) Appl. No.: 17/419,480

(22) PCT Filed: Dec. 20, 2019

(86) PCT No.: PCT/US2019/067916
§ 371 (c)(1),
(2) Date: Jun. 29, 2021

(87) PCT Pub. No.: WO2020/142275
PCT Pub. Date: Jul. 9, 2020

(65) Prior Publication Data
US 2022/0033487 A1 Feb. 3, 2022

Related U.S. Application Data

(60) Provisional application No. 62/786,821, filed on Dec. 31, 2018.

(51) Int. Cl.
*C07K 16/24* (2006.01)

(52) U.S. Cl.
CPC ........ *C07K 16/244* (2013.01); *C07K 2317/14* (2013.01); *C07K 2317/21* (2013.01); *C07K 2317/31* (2013.01); *C07K 2317/41* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,868,116 A | 9/1989 | Morgan et al. | |
| 4,980,286 A | 12/1990 | Morgan et al. | |
| 5,013,556 A | 5/1991 | Woodle et al. | |
| 5,308,341 A | 5/1994 | Chanoch | |
| 5,641,640 A | 6/1997 | Hanning | |
| 5,807,715 A | 9/1998 | Morrison et al. | |
| 6,146,361 A | 11/2000 | DiBiasi et al. | |
| 6,192,891 B1 | 2/2001 | Gravel et al. | |
| 6,200,296 B1 | 3/2001 | Dibiasi et al. | |
| 6,277,099 B1 | 8/2001 | Strowe et al. | |
| 6,302,855 B1 | 10/2001 | Lav et al. | |
| 7,556,615 B2 | 7/2009 | Pettis et al. | |
| 11,719,704 B2 | 8/2023 | Robblee | |
| 2011/0045581 A1 | 2/2011 | Collao Olivares et al. | |
| 2013/0123126 A1 | 5/2013 | Collins et al. | |
| 2014/0271622 A1 | 9/2014 | Prentice | |
| 2014/0359902 A1 | 12/2014 | Ariaans et al. | |
| 2015/0158907 A1 | 6/2015 | Zhou et al. | |
| 2015/0204884 A1 | 7/2015 | Robblee et al. | |
| 2015/0252108 A1 | 9/2015 | Washburn et al. | |
| 2016/0032232 A1 | 2/2016 | Khan | |
| 2016/0289628 A1 | 10/2016 | Cizek et al. | |
| 2019/0025325 A1 | 1/2019 | Robblee | |
| 2020/0199525 A1 | 6/2020 | Boon et al. | |
| 2021/0222109 A1 | 7/2021 | Yin et al. | |
| 2022/0033487 A1 | 2/2022 | Zang | |
| 2022/0081479 A1 | 3/2022 | Zang | |
| 2023/0324406 A1 | 10/2023 | Robblee | |

FOREIGN PATENT DOCUMENTS

| | | |
|---|---|---|
| CN | 105378086 A | 3/2016 |
| CN | 105779394 A | 7/2016 |
| CN | 106029871 A | 10/2016 |
| CN | 107109455 A | 8/2017 |
| WO | 198902468 A1 | 3/1989 |
| WO | 198907136 A2 | 8/1989 |
| WO | 199111508 A1 | 8/1991 |
| WO | 199207573 A1 | 5/1992 |
| WO | 200230954 A1 | 4/2002 |
| WO | 2004060407 A1 | 7/2004 |
| WO | 2008128216 A1 | 10/2008 |
| WO | 2008128218 A1 | 10/2008 |
| WO | 2008128219 A1 | 10/2008 |
| WO | 2008128220 A1 | 10/2008 |
| WO | 2008128221 A1 | 10/2008 |
| WO | 2008128222 A1 | 10/2008 |
| WO | 2008128225 A1 | 10/2008 |
| WO | 2008128227 A1 | 10/2008 |
| WO | 2008128228 A1 | 10/2008 |
| WO | 2008128230 A1 | 10/2008 |
| WO | 2008130924 A1 | 10/2008 |
| WO | 2008130926 A2 | 10/2008 |
| WO | 2010071817 A2 | 6/2010 |

(Continued)

OTHER PUBLICATIONS

Loebrich et al., "Comprehensive manipulation of glycosylation profiles across development scales", vol. 11, pp. 335-359; published online on Oct. 2018 (Year: 2019).*

Hamm, M. et al., Characterization of N-Linked Glycosylation in a Monoclonal Antibody Producted in NS0 Cells Using Capillary Electrophoresis with Laser-Induced Fluroescence Detection, Pharmaceuticals, 6:393-406 (2013).

Haselberg, R. et al., Heterogeneity assessment of antibody-derived therapeutics at the intact and middle-up level by low-flow sheathless capillary electrophoresis-mass spectrometry, Analytica Chimica Acta, 1044:181-190 (2018).

International Search Report for PCT/US2019/067916 (Methods of Producing Ustekinumab, Dec. 20, 2019) received by ISA/US, 5 pages (Apr. 14, 2020).

Liu, Liming, Antibody Glycosylation and Its Impact on the Pharmacokinetics and Pharmcodynamics of Monoclonal Antibodies and Fc-Fusion Proteins, Journal of Pharmaceutical Sciences, 104:1866-1884 (2015).

(Continued)

*Primary Examiner* — Michelle F. Paguio Frising (74) *Attorney, Agent, or Firm* — Troutman Pepper Locke LLP; Mark R. Bell; Megan T. O'Gara (57) ABSTRACT

Methods of manufacturing an ustekinumab product with a target level of one or more glycans are described.

16 Claims, 4 Drawing Sheets

Specification includes a Sequence Listing.

(56) References Cited

FOREIGN PATENT DOCUMENTS

| WO | 2010071824 A2 | 6/2010 |
| --- | --- | --- |
| WO | 2010085251 A1 | 7/2010 |
| WO | 2010089151 A1 | 8/2010 |
| WO | 2011069056 A2 | 6/2011 |
| WO | 2011127322 A1 | 10/2011 |
| WO | 2013181575 A2 | 12/2013 |
| WO | 2013181586 A2 | 12/2013 |
| WO | 2014193973 A2 | 12/2014 |
| WO | 2015105926 A1 | 7/2015 |
| WO | 2017021493 A1 | 2/2017 |
| WO | 2017117218 A1 | 7/2017 |
| WO | 2017194605 A1 | 11/2017 |
| WO | WO-2018/024770 A1 | 2/2018 |
| WO | 2020051042 A1 | 3/2020 |
| WO | WO-2020/142275 A1 | 7/2020 |

OTHER PUBLICATIONS

Liu, Liming, Pharmacokinetics of monoclonal antibodies and Fc-fusion proteins, Protein Cell, 9(1):15-32 (2018).

Mimura, Y. et al., Glycosylation engineering of therapeutic IgG antibodies: challenges for the safety, functionality and efficacy, Protein Cell, 9(1):47-62 (2018).

Written Opinion for PCT/US2019/067916 (Methods of Producing Ustekinumab, Dec. 20, 2019) received by ISA/US, 11 pages (Apr. 14, 2020).

Zhang, P. et al., Challenges of glycosylation analysis and control: an integrated approach to producing optimal and consistent therapeutic drugs, Drug Discovery Today, 21(5):740-765 (2016).

Alfthan et al., "Properties of a Single-Chain Antibody Containing Different Linker Peptides" Protein Eng. (1995) vol. 8, Issue 7, pp. 725-731.

Corrected Notice of Allowability for U.S. Appl. No. 16/067,411 dated Jun. 14, 2023.

European Search Report for European Patent Application No. 16882558.6 dated Jul. 8, 2019.

European Search Report for European Patent Application No. 19857341.2 dated Jun. 7, 2022.

European Search Report for European Patent Application No. 19907232.3 dated Aug. 18, 2022.

Fan et al., "A Multi-Pronged Investigation into the Effect of Glucose Starvation and Culture Duration on Fed-Batch CHO Cell Culture," Biotech. & Bioeng. (2015) vol. 108, No. 10, pp. 2172-2184.

Final Office Action for U.S. Appl. No. 16/067,411 dated Oct. 7, 2022.

Fournier et al., "A Review of Glycan Analysis Requirements," BioPharm International (Oct. 1, 2015) vol. 28(10), pp. 1-10.

Gilar et al., "Rapid Assessment of Molecular Similarity between a Candidate Biosimilar and an Innovator Monoclonal Anitbody Using Complementary LC-MS Methods," BioPharm International (Aug. 2, 2010) vol. 2010(1), pp. 1-5.

Hallewell et al., "Genetically Engineered Polymers of Human CuZn Superoxide Dismutase," J. Biol. Chem. (1989) vol. 264, No. 9, pp. 5260-5268.

McCracken et al., "Control of Galactosylated Glycoforms Distribution in the Cell Culture System," Biotechnology Progress (2014) vol. 30, No. 3, pp. 547-553.

Notice of Allowance for U.S. Appl. No. 16/067,411 dated Mar. 8, 2023.

Pacis et al., "Effects of Cell Culture Conditions on Anitbody N-Linked Glycosylation—What Affects High Mannose 5 Glycoform," Biotech. & Bioeng. (2011) vol. 108, No. 10, pp. 2348-2358.

Restelli et al., "The Effect of Cell Culture Parameters on Protein Glycosylation," Cell Engineering (Jan. 1, 2002) vol. 3, pp. 61-92.

Zhang et al., "Glycan Analysis of Therapeutic Glycoproteins," mAbs (Nov. 24, 2015) vol. 8, No. 2, pp. 205-215.

Chao et al., "Research of Therapeutic Antibody Glycosylation and Its Applications," Shandong Chemical Industry (2013) vol. 42(10), pp. 54-57, 61.

European Search Report for European Patent Application No. 232018010 dated Feb. 16, 2024.

Ahn et al., "Separation of 2-aminobenzamide labeled glycans using hydrophilic interaction chromatography columns backed with 1.7 ?m sorbent" Chrom. B, (2010) 878:403-408.

Anumula, "Advances in fluorescence derivatization methods for high-performance liquid chromatographic analysis of glycoprotein carbohydrates" Anal. Biochem., (2006) 350(1):1-23.

Bitter et al., "Expression and Secretion Vectors for Yeast" Methods in Enzymol. (1987) 153:516-544.

Chen et al., "Gas-phase oligosaccharide nonreducing end (GONE) sequencing and structural analysis by reversed phase hplc/mass spectrometry with polarity switching" J. Am. Soc. Mass Spectrom., (2009) 20:1821-1833.

Chen, "Analysis of N-glycan from recominant immunoglobulin G by on-line reversed-phase high-performance liquid chromatography/mass spectrometry", Anal. Biochem., (2007) 370:147-161.

D'Angelo et al., "Many Routes to an Antibody Heavy-Chain CDR3: Necessary, Yet Insufficient, for Specific Binding", Front Immunol. (2018) 8;9:395. doi:103389/fimmu.2018.00395.eCollection 2018.

Dick et al. "C-terminal lysine variants in fully human monoclonal antibodies: Investigation of test methods and possible causes", Biotechnology and Bioengineering (2008) 100:1132-1143.

Edwards et al., "The Remarkable Flexibiltiy of the Human Antibody Repertoire; Isolation of Over One Thousand Different Antibodies to a Single Protein, BLyS", J Mol Biol (2003) 14; 334(1): pp. 103-118.

European Medicines Agency Evaluation of Medicines for Human Use "Assment Report for Stelara", Retrieved from the Internet:// www.ema.europa.eu/documents/assessment-report/stelara-epar-public-assessment-report_en.pdf, retrieved on Jun. 24, 2019.

Forrer et al., "Chip-based gel electrophoreses method for the quantification of hallf-antibody species in IgG4 and their by- and degradation products", Anal. Biochem., (2004) 334:81-88.

Ghaderi, et al., Production platforms for biotherapeutic glycoprotins. Occurence, inpact, and challenges of non-human sialylation, Biotechnol Genet Eng Rev., (2012) 28:147-75.

Goel et al., "Plasticity within the Antigen-Combining Site May Manifest as Molecular mimicry in the Humoral Immune Response" J Immunol (2004) 173(12):7358-67.

Goetze et al., "High-mannose glycans on the Fc region of therapeutic IgG antibodies increase serum clearance in humans", Glycobiol (2011) 21:949-959.

Gooch et al., "Shear Sensitivity in animal cell culture" Current Opinion in Biotechnology (1993) 4:193-196.

Hara et al., "Determination of Mono-O-acetylated N-Acetylneuraminic", Anal Biochem., (1989) 179:162-166.

Hincal, "An Introduction To Safety Issues In Biosimilars/Follow-On Biopharmaceuticals", J. Med. CBR Def. (2009) 7:1-18.

Hokke et al., "Sialylated carbohydrate chains of recombinant human glycoproteins expressed in Chiese hamster ovary cells contain traces of N-glycolylneuraminic acid" FEBS Lett., (1990) 275:9-14.

International Search Report for PCT/US2016/068871 issued by ISA/US, 9 gages (Apr. 13, 2017).

International Search Report for PCT/US2019/048594 issued by ISA/US, Nov. 15, 2019.

Janeway et al., "Immuno Biology the Immune System in Hearlth and Disease", Immunobiology, 3rd edition, (1997) Publishing Inc., pp. 3:1-3:11.

Kanyavuz et al., "Breaking the law: unconventional strategies for antibody diversification" Nat Rev Immunol (2019) 19(6):355-368. doi:10.1038/S41577-019-0126-7.

Lloyd et al., "Modelling the human immune response: performance of 10" Human antibody repertoire against a broad panel of therapeutically relevant antigens", Protein Eng Des Sel (2009) 22(3): pp. 159-168, doi: 10.1093/protein/gzn058.epub Oct. 29, 2008.

Logan et al., "Adenovirus tripartite leader sequence enhances translation of mRNAs late after infection", Proc. Natl. Acad. Sci. USA (1984) 8 1:3655-3659.

Non-final Office Action mailed Apr. 12, 2022 received in U.S. Appl. No. 16/067,411.

Nowicki, "Basic Facts about Biosimilars", Kidney Blood Press (2007) 30:267-272.

(56) References Cited

OTHER PUBLICATIONS

Roger, "Biosimilars: current status and future directions", Expert Opin. Bio. Ther., (2010) 10(7):1011-1018.

Rudikoff et al., "Single Amino Acid Substitution Altering Antigen-Binding Specificity", Proc Natl Acad Sci USA (1982) 79(6): 1979-83.

Sanchez-De Melo, et al., N-glycosylation profile analysis of Trastuzumab biosimilar candidates by Normal Phase Liquid Chromatography and MALD-TOF MS approaches, J Proteomics, (2015) 12(ptB):225-33.

Schellekens et al., "Clinical comparability and European biosimilar regulations", Nat Biotechnol . . . (2010) 28:28-31.

Bekhon et al., "Biosimilars: an overview" Biosimilars, (2011) 1:1-11.

Shang et al., "Development and Application of a Robust N-Glycan Profiling Method for Heightened Characterization of Monoclonal Antibodies and Related Glycoproteins" J. Pharm. Sciences, (2014) 103:1967-1978.

Written opinion for PCT/US2016/068871, issued by ISA/US, 9 pages Apr. 13, 2017.

Written opinion for PCT/US2019/048594, issued by ISA/US, Nov. 15, 2019.

Xie et al., "Rapid comparison of a candidate biosimilar to an innovator monoclonal antibody with advanced liquid chormatography and mass spectrometry technologies" (2010) mAbs, 2:379-394.

Zhu et al., "NSO Cell Damage by High Gas Velocity Sparging in Protein-Free and Cholesterol-Free Cultures" Biotechnology and Bioengineering, (2008) vol. 101, No. 4, pp. 751-760.

Amano et al., "Mammalian cell culture tank design by computational fluid dynamics," Hitachi Review (2007) vol. 89(5), pp. 34-37.

Non-final Office Action mailed Apr. 24, 2024 received in U.S. Appl. No. 17/273,004.

Cong et al., "Recent Advances on the Analysis of Glycosylation of Therapeutic Monoclonal Antibodies," Chinese Journal of Chromatography (2016) vol. 34, No. 12, pp. 1186-1191. (English Abstract Only).

Final Office Action for U.S. Appl. No. 17/273,004 dated Nov. 19, 2024.

Matanguihan et al., "Solution to the High Dissolved CO2 Problem in High-Density Perfusion Culture of Mammalian Cells," Animal Cell Technology: From Target to Market (2001) pp. 399-400.

\* cited by examiner

SEQUENCE LISTING

<160> NUMBER OF SEQ ID NOS: 2

<210> SEQ ID NO 1
<211> LENGTH: 449
<212> TYPE: PRT
<213> ORGANISM: Homo sapiens

<400> SEQUENCE: 1

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110

Thr Leu Val Thr Val Ser Ser Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 2
<211> LENGTH: 214
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95
```

```
Thr Phe Gly Gln Gly Thr Lys Leu Glu Ile Lys Arg Thr Val Ala Ala
            100             105                 110

Pro Ser Val Phe Ile Phe Pro Pro Ser Asp Glu Gln Leu Lys Ser Gly
        115             120                 125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155                 160

Glu Ser Val Thr Glu Gln Asp Ser Lys Asp Ser Thr Tyr Ser Leu Ser
            165             170                 175

Ser Thr Leu Thr Leu Ser Lys Ala Asp Tyr Glu Lys His Lys Val Tyr
            180             185                 190

Ala Cys Glu Val Thr His Gln Gly Leu Ser Ser Pro Val Thr Lys Ser
        195             200                 205

Phe Asn Arg Gly Glu Cys
        210
```

METHODS OF PRODUCING USTEKINUMAB

CROSS-REFERENCE TO RELATED APPLICATIONS

This application is a 371 national stage application of International Application Number PCT/US2019/06791, filed Dec. 20, 2019, which claims the benefit of U.S. Provisional Application No. 62/786,821, filed Dec. 31, 2018, which are hereby incorporated by reference in their entireties.

SEQUENCE LISTING

The instant application contains a Sequence Listing which has been filed electronically in ASCII format and is hereby incorporated by reference in its entirety. Said ASCII copy, created on Jun. 22, 2021, is named MPI5168USPCT1SEQLIST.TXT and is 6, 117 bytes in size.

BACKGROUND

Therapeutic antibodies are an important class of therapeutic biological products. Antibody glycosylation and glycan composition can impact antibody activity and effector functions. There remains an ongoing need for improved methods for controlling the glycan profile of antibody products.

SUMMARY OF THE INVENTION

The present disclosure provides process levers for producing (e.g., manufacturing) ustekinumab with a target level of one or more glycans. The present disclosure provides the insight that a relationship between galactose concentration in a culture media and time of culturing can be used as a process lever for controlling a target level of one or more glycans (e.g., galactosylation) of ustekinumab in a culture. The present disclosure identifies an inverse relationship between culture time and galactose concentration in culture media in controlling a target level of one or more glycans (e.g., galactosylation).

In certain aspects, the disclosure provides methods of manufacturing ustekinumab with a target level of one or more glycans. Such methods can include providing (e.g., producing, expressing (e.g., in small scale or large scale cell culture) and/or manufacturing) or obtaining (e.g., receiving and/or purchasing from a third party (including a contractually related third party or a non-contractually-related (e.g., an independent) third party)) an ustekinumab test protein (e.g., an ustekinumab drug substance, e.g., a preparation of ustekinumab drug substance, e.g., a batch of test ustekinumab dug substance).

In some instances, the disclosure provides methods of manufacturing a pharmaceutical composition comprising ustekinumab having a target level of one or more glycans, the method comprising: selecting a level of galactose and a time for cell culture, where the level of galactose and the time are inversely related; culturing a population of cells genetically engineered to express ustekinumab under conditions comprising the selected level of galactose and time; harvesting ustekinumab expressed by the population of cells, thereby producing the preparation of ustekinumab; and purifying, concentrating, and/or formulating the ustekinumab preparation to produce pharmaceutical composition comprising ustekinumab if the preparation meets the target level of one or more glycans. In some embodiments, the target level of one or more glycans is a target level of a glycan selected from the group consisting of G0F, sialylated glycan, and G2F. In some embodiments, the target level of one or more glycans is a target level of G0F.

In some instances, the disclosure provides methods of manufacturing a pharmaceutical composition comprising ustekinumab having a target level of G0F glycan, the method comprising: selecting a target level of G0F glycan; selecting a level of galactose and a time for cell culture to provide the selected target level of G0F, where the level of galactose and the time are inversely related; culturing a population of cells genetically engineered to express ustekinumab under conditions comprising the selected level of galactose and time; harvesting ustekinumab expressed by the population of cells, thereby producing the preparation of ustekinumab; and purifying, concentrating, and/or formulating the ustekinumab preparation to produce pharmaceutical composition comprising ustekinumab if the preparation meets the target level of G0F glycan.

In some instances, the disclosure provides methods of producing an ustekinumab drug product having a target level of one or more glycans, the method comprising: culturing a population of cells genetically engineered to express ustekinumab under conditions, where the conditions are characterized by parameters including a selected level of galactose and a time for cell culture, and where the level of galactose and the time are inversely related; harvesting ustekinumab expressed by the cell, thereby producing an ustekinumab preparation; and purifying, concentrating, and/or formulating the ustekinumab preparation to produce an ustekinumab drug product if the ustekinumab preparation meets the target level of one or more glycans. In some embodiments, the target level of one or more glycans is a target level of a glycan selected from the group consisting of G0F, sialylated glycan, and G2F. In some embodiments, the target level of one or more glycans is a target level of G0F.

In some embodiments, provided methods include culturing a population of mammalian cells that are genetically engineered to express ustekinumab. In some embodiments, mammalian cells are selected from: CHO cells, HEK 293 cells, fibrosarcoma HT 1080 cells, PER.C6 cells, CAP cells, HKB-11 cells, HuH-7 cells, NS0 cells and SP 2/0 cells.

In some embodiments, in the provided methods the culturing step is performed using continuous culture process. In some embodiments, provided methods include culturing that is performed using a perfusion culture process (e.g., an alternating tangential flow filter (ATF)-based perfusion culture process). In some certain embodiments, provided methods include culturing mammalian cells that are genetically engineered to express ustekinumab (e.g., SP 2/0 cells that express ustekinumab) by a perfusion culture process.

In some embodiments, provides methods including harvesting ustekinumab expressed by the cells at two or more times within the range of time of the time for cell culture.

In some embodiments, a target level of G0F glycan is within a range of 20% to 80% G0F relative to total glycan. In some embodiments, a target level of G0F glycan is within a range of 25% to 65% G0F relative to total glycan.

In some embodiments, provided methods are directed to manufacturing and/or producing ustekinumab having a target level of G0F glycan within a range of 20% up to 40% G0F relative to total glycan. In some embodiments, a method for achieving ustekinumab having a target level of G0F glycan within a range of 20% up to 40% G0F relative to total glycan includes a selected level of galactose at 0 mM and a time for cell culturing is within a range of 7 days to 15 days.

In some embodiments, provided methods are directed to manufacturing and/or producing ustekinumab having a target level of G0F glycan within a range of 40% to 80% G0F relative to total glycan. In some embodiments, a method for achieving ustekinumab having a target level of G0F glycan within a range of 40% to 80% G0F relative to total glycan include a selected level of galactose within a range of 15 mM to 30 mM and a time for cell culture that is within a range of 16 days to 60 days. In some certain embodiments, a time for cell culturing is within a range of 25 days to 42 days.

In some embodiments, provided methods include selecting a target level of G0F glycan. In some embodiments, a target level of G0F glycan is within a range of 20% to 80% G0F relative to total glycan. In some certain embodiments, a target level of G0F glycan within a range of 20% up to 40% G0F relative to total glycan, where the method includes a selected level of galactose at 0 mM and a time for cell culture that is within a range of 7 days to 15 days. In some certain embodiments, a target level of G0F glycan within a range of 40% to 80% G0F relative to total glycan, where the method includes a selected level of galactose within a range of 15 mM to 30 mM and a time for cell culture that is within a range of 16 days to 60 days.

In some embodiments, provided methods a selected level of galactose is controlled throughout the culturing step (e.g., controlled during culturing from t=0 until harvest).

In some embodiments, provided methods further include measuring a level of G0F glycan. In some embodiments, if the measured level of G0F glycan is within a range of 20% to 80% G0F relative to total glycan (e.g., within a range of 20% up to 40% G0F relative to total glycan, e.g., within a range of 40% to 80% G0F relative to total glycan), then a step of purifying, concentrating, and/or formulating the ustekinumab preparation is performed.

These, and other aspects of the invention, are described in more detail below and in the claims.

BRIEF DESCRIPTION OF THE DRAWINGS

The Drawing included herein, which is composed of the following Figures, is for illustration purposes only and not for limitation.

FIG. 1 depicts comparison of glycan profiles of various preparations and sources of ustekinumab. Abundance of G0F glycan is provided in the upper left panel; abundance of G1F-A glycan is provided in the upper right panel; abundance of G1F-B glycan is provided in the lower left panel; and total sialylation provided in the lower right panel. Solid circles represent reference protein products ("RPPs") from the U.S. (black solid circles) and Europe (shaded solid circles). Symbols in the right-most portion of each panel represent ustekinumab test preparations cultured at different volumes. Solid shaded squares depicting samples cultured at 3 L, open squares depicting samples from satellite culture, solid triangles depicting samples cultured at 100 L, and solid diamonds depicting samples cultured at 250 L. The relative abundance of each glycan depicted in its respective panel, with samples depicted in each panel sorted into four groups, walking along the x-axis from left to right: Group 1 RPPs from 90 mg/ml reference samples (left most), Group 2 RPPs from 90 mg/ml reference samples (second from left), 5 mg/mL RPPs (third from left) and ustekinumab test products (right most).

FIGS. 3A-3B depicts comparisons of major glycan profiles and charge variants between various culture conditions. Walking along the x-axis of each panel from left to right depicts: Group 1 RPPs (left-most), Group 2 RPPs, ustekinumab cultured at 3 L DS, ustekinumab cultured at 100 L DS, ustekinumab cultured at 250 L DS, NCM-2 ustekinumab preparation, and NCM-1 ustekinumab preparation (right-most).

CERTAIN DEFINITIONS

In general, terminology used herein is in accordance with its understood meaning in the art, unless clearly indicated otherwise. Explicit definitions of certain terms are provided below; meanings of these and other terms in particular instances throughout this specification will be clear to those skilled in the art from context.

In order that the present invention may be more readily understood, certain terms are first defined below. Additional definitions for the following terms and other terms are set forth throughout the specification.

As used herein, the terms "about" or "approximately," as applied to one or more values of interest, refers to a value that is similar to a stated reference value. In certain embodiments, the terms "about" or "approximately" refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

The terms "control, controlled, controlling," as used herein in reference to controlling a target level of one or more glycans (e.g., galactose, e.g., G0F) of ustekinumab means selecting, maintaining and/or adjusting one or more culture conditions for production of ustekinumab. Adjusting can including increasing or decreasing one or more culture conditions for production of ustekinumab. As used herein, a controlled target level of one or more glycans relates to production of ustekinumab with a desired level of one or more glycans that has minimal product drift. In some embodiments, a controlled target level of G0F will vary no more than 20%, 15%, 10%, or 5% between samples in the same production run and/or batch. In some embodiments, controlling a target level of one or more glycan ensures consistency in the production of ustekinumab (e.g., batch to batch consistency, consistency throughout samples from any particular production process).

As used herein, a "glycan" refers to a compound comprising at least one sugar residue (e.g., monosaccharide). Glycans can be monomers or polymers of sugar residues, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'-sulfo N-acetylglucosamine, etc). The term glycan includes homopolymers and heteropolymers of sugar residues. The term "glycan" also encompasses a glycan component of a glycoconjugate (e.g., a glycoprotein, glycolipid, proteoglycan, etc.). The term also encompasses free glycans, including glycans that have been cleaved or otherwise released from a glycoconjugate.

As used herein, a "galactosylated glycan" refers to a glycan that includes at least one galactose sugar residue. In some embodiments, a galactosylated glycan is a G1, G2, G1F, G2F, A1, and/or A2 glycan. A non-galactosylated glycan includes G0F or G0. In some embodiments, a target level of galactosylated glycan may refer to the presence of galactosylated glycan (e.g., G2F) and/or a target level of non-galactosylated glycan (e.g., G0F).

The term "isolated," as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

As used herein, "process lever" refers to an element of a culture process (e.g., one or more culture conditions) that can be controlled in order to increase or decrease the abundance of one or more glycans on an antibody product. The present disclosure provides a novel process lever that is a specified relationship between galactose concentration in the culture media and culture time. As described herein, an inverse relationship between galactose concentration in a culture media and the time of culture in the culture media can be used as a process lever to produce ustekinumab with a target level of one or more glycans (e.g., galactosylation).

In some embodiments, a process lever includes a selected a level of galactose and time for cell culture to control level of one or more glycans (e.g., galactosylation, e.g., G0F) of ustekinumab (e.g., level of one or more glycans in a ustekinumab culture or preparation).

As used herein, an "N-glycosylation site of an Fc region" refers to an amino acid residue within an Fc region to which a glycan is N-linked. In some certain embodiments, a N-glycosylation site of ustekinumab is located in a heavy chain at position Asn299.

In general, a "protein," as used herein, is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

As used herein "recovering" refers to the process of rendering an agent or entity substantially free of other previously-associated components, for example by isolation, e.g., using purification techniques known in the art. In some embodiments, an agent or entity is recovered from a natural source and/or a source comprising cells.

As used herein, "sample(s)" refer to separately procured samples. In some embodiments, evaluation of separate samples includes evaluation of samples from the same culture run (e.g., at different time points during preparation) or from different culture runs (e.g., different rounds of culture).

"Target value or target level", as used herein, refers to a predetermined level of one or more particular glycans, such as galactosylated glycans and/or sialylated glycans. In some embodiments, a target value is a level of one or more particular glycans, such as galactosylated glycans (e.g., G0, G1, G2, G0F, G1F, G2F or combinations) and/or sialylated glycans (e.g., monosialylated, disialylated, or combinations), in a reference ustekinumab product or described in a specification or master batch record for a pharmaceutical product. In some certain embodiments, a target value is a level of G0F glycans in an ustekinumab product.

In some embodiments, a target value refers to an absolute level of (e.g., number of moles of) one or more glycans (e.g., galactosylated glycans (e.g., one or more species of galactosylated glycans) and/or sialylated glycans (e.g., one or more species of sialylated glycans)) in a ustekinumab preparation. In some embodiments, a target value refers to a level of one or more glycans (e.g., galactosylated glycans (e.g., one or more species of galactosylated glycans) and/or sialylated glycans (e.g., one or more species of sialylated glycans)) in a ustekinumab preparation relative to total level of glycans in the ustekinumab preparation. In some embodiments, a target value is expressed as a "percent", which refers to the number of moles of one or more glycans (e.g., Fc glycans) relative to total moles of glycans (e.g., Fc glycans) in a ustekinumab preparation. In some embodiments, "percent" refers to the number of moles of one or more PNGase F-released Fc glycans relative to total moles of PNGase F-released Fc glycans detected.

The term "ustekinumab preparation" as used herein refers to a mixture of ustekinumab proteins obtained according to a particular production method. Ustekinumab proteins in an ustekinumab preparation includes multiple copies of ustekinumab (i.e., having the same or substantially the same amino acid sequence) but have a mixture of glycans associated with the protein. In some instances, an ustekinumab preparation is prepared using a method and/or system as provided herein. Production methods can include a recombinant preparation step using cultured cells that have been engineered to express ustekinumab (or to express ustekinumab at a relevant level or under relevant conditions). In some embodiments, a production method may include an isolation step in which ustekinumab is isolated from certain components of the engineered cells (e.g., by lysing the cells and pelleting the protein component by centrifugation). In some embodiments, production method may also include a purification step in which ustekinumab is separated (e.g., by chromatography) from other cellular components, e.g., other proteins or organic components that were used in earlier steps. It will be appreciated that these steps are non-limiting and that any number of additional productions steps may be included. Different ustekinumab preparations may be prepared by the same production method but on different occasions (e.g., different runs or preparations). Alternatively, different ustekinumab preparations may be prepared by different production methods. Two production methods may differ in any way (e.g., expression vector, engineered cell type, culture conditions, isolation procedure, purification conditions, etc.).

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way.

DETAILED DESCRIPTION OF CERTAIN EMBODIMENTS

The present disclosure describes, at least in part, the discovery of process levers for producing ustekinumab having targeted levels of one or more glycans (e.g., galactosylation, e.g., G0F glycans). Controlling glycan composition and levels during antibody production is a continuing challenge. Glycosylation of therapeutic antibodies can impact their safety and/or efficacy. (Zhang et al. (2016) Drug Discovery Today 21 (5): 740-765). Accordingly, it is important to be able to ensure consistency of glycan composition in the production of ustekinumab (e.g., batch to batch consistency, consistency throughout samples from any particular production process). During characterization of ustekinumab reference protein products ("RPPs"), two distinct glycan populations of ustekinumab RPPs were observed.

The present disclosure describes the development of levers for controlling glycan composition during manufacture of ustekinumab. Process levers are described herein to produce ustekinumab with target levels of particular glycans, including each of the RPPs glycan profiles identified. In the course of developing levers as described, the present disclosure identified a relationship between galactose concentration in a culture media and time of culturing. The present disclosure provides the insight that a relationship between galactose concentration in a culture media and time of culturing (e.g., continuously culturing) can be used as a process lever for controlling a target level of one or more glycans (e.g., galactosylation) of ustekinumab in a culture.

The present disclosure further provides the insight that the for controlling the glycan level (e.g., galactosylation), a relationship between a level of galactose and time (i.e., duration of culturing) are inversely related. Culturing methods of the present disclosure for controlling glycan compositions include continuous culture methods (e.g., perfusion culture).

Ustekinumab

The present disclosure provides, in part, methods and processes for manufacturing, preparing, controlling or otherwise generating ustekinumab with particular glycan profiles.

Ustekinumab is an antibody that specifically binds to the p-40 subunit of both IL-12 and IL-23. Ustekinumab has been studied in a number of human diseases including psoriasis, psoriatic arthritis, Crohn's disease and multiple sclerosis.

In some embodiments, ustekinumab includes HCDR1, HCDR2, and HCDR3 sequences that differ by no more than 3 amino acid residues from the HCDR sequences as set forth in SEQ ID NO.: 1 and LCDR1, LCDR2, and LCDR3 sequences that differ by no more than 3 amino acid residues from the LCDR sequences as set forth in SEQ ID NO.: 2. In some embodiments, ustekinumab includes HCDR1, HCDR2, and HCDR3 sequences that differ by no more than 2 amino acid residues or by no more than 1 amino acid residue from the HCDR sequences as set forth in SEQ ID NO.: 1 and LCDR1, LCDR2, and LCDR3 sequences that differ no more than 2 amino acid residues or by no more than 1 amino acid residue from the LCDR sequences as set forth in SEQ ID NO.: 2. In some embodiments, ustekinumab includes a heavy chain variable domain that differs by no more than 3 amino acid resides from the sequence as set forth in SEQ ID NO.: 1 and a light chain variable domain that differs by no more than 3 amino acid resides from the sequence as set forth in SEQ ID NO.: 2. In some embodiments, ustekinumab includes a heavy chain that includes a sequence that differs by no more than 5 amino acids from the sequence as set forth in SEQ ID NO.: 1 and a light chain that includes a sequence that differs by no more than 5 amino acid resides from the sequence of SEQ ID NO.: 2.

In some embodiments, ustekinumab includes HCDR1, HCDR2, and HCDR3 sequences as set forth in SEQ ID NO.: 1 and LCDR1, LCDR2, and LCDR3 sequences as set forth in SEQ ID NO.: 2. In some embodiments, ustekinumab includes a heavy chain variable domain as set forth in SEQ ID NO.: 1 and a light chain variable domain as set forth in SEQ ID NO.: 2. In some embodiments, ustekinumab includes a heavy chain comprising a sequence of SEQ ID NO.: 1 and/or a light chain comprising a sequence of SEQ ID NO.: 2.

ustekinumab heavy chain sequence (bold indicates variable domain sequence with CDR sequences underlined)

SEQ ID NO.: 1
EVQLVQSGAEVKKPGESLKISCKGSGYSFTTYWLGWVRQMPGKGLDWIGI

MSPVDSDIRYSPSFQGQVTMSVDKSITTAYLQWNSLKASDTAMYYCARRR

PGQGYFDFWGQGTLVTVSSSSTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLEPPKPK

-continued

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK ustekinumab light chain sequence (bold indicates
variable domain sequence with CDR sequences
underlined)
SEQ ID NO.: 2
DIQMTQSPSSLSASVGDRVTITC<u>RASQGISSWLA</u>WYQQKPEKAPKSLIYA

ASSLQSGVPSRFSGSGSGTDFTLTISSLQPEDFATYYC<u>QQYNIYPYT</u>FGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSENRGEC

Culture Methods

In some instances, the disclosure provides methods of manufacturing a pharmaceutical composition comprising ustekinumab having a target level of one or more glycans, the method comprising: selecting a level of galactose and a time for cell culture, where the level of galactose and the time are inversely related; culturing a population of cells genetically engineered to express ustekinumab under conditions comprising the selected level of galactose and time; harvesting ustekinumab expressed by the population of cells, thereby producing the preparation of ustekinumab; and purifying, concentrating, and/or formulating the ustekinumab preparation to produce pharmaceutical composition comprising ustekinumab if the preparation meets the target level of one or more glycans. In some embodiments, the target level of one or more glycans is a target level of a glycan selected from the group consisting of G0F, sialylated glycan, and G2F. In some embodiments, the target level of one or more glycans is a target level of G0F.

In some instances, the disclosure provides methods of producing an ustekinumab drug product having a target level of one or more glycans, the method comprising: culturing a population of cells genetically engineered to express ustekinumab under conditions, where the conditions are characterized by parameters including a selected level of galactose and a time for cell culture, and where the level of galactose and the time are inversely related; harvesting ustekinumab expressed by the cell, thereby producing an ustekinumab preparation; and purifying, concentrating, and/or formulating the ustekinumab preparation to produce an ustekinumab drug product if the ustekinumab preparation meets the target level of one or more glycans. In some embodiments, the target level of one or more glycans is a target level of a glycan selected from the group consisting of G0F, sialylated glycan, and G2F. In some embodiments, the target level of one or more glycans is a target level of G0F.

In some embodiments, a target level of G0F glycan is within a range of 20% to 80% G0F relative to total glycan. In some embodiments, a target level of G0F glycan is within a range of 25% to 65% G0F relative to total glycan.

In some embodiments, provided methods are directed to manufacturing and/or producing ustekinumab having a target level of G0F glycan within a range of 20% up to 40% G0F relative to total glycan. In some embodiments, a method for achieving ustekinumab having a target level of G0F glycan within a range of 20% up to 40% G0F relative to total glycan includes a selected level of galactose at 0 mM and a time for cell culture that is within a range of 7 days to 15 days.

In some embodiments, provided methods are directed to manufacturing and/or producing ustekinumab having a target level of G0F glycan within a range of 40% to 80% G0F relative to total glycan. In some embodiments, a method for achieving ustekinumab having a target level of G0F glycan within a range of 40% to 80% G0F relative to total glycan include a selected level of galactose within a range of 15 mM to 30 mM and a time for cell culture that is within a range of 16 days to 60 days. In some certain embodiments, a time for cell cultures is within a range of 25 days to 42 days.

In some embodiments, provided methods further include selecting a target level of G0F glycan. In some embodiments, a target level of G0F glycan is within a range of 20% to 80% G0F relative to total glycan. In some certain embodiments, a target level of G0F glycan within a range of 20% up to 40% G0F relative to total glycan, where the method includes a selected level of galactose at 0 mM and a time for cell culture that is within a range of 7 days to 15 days. In some certain embodiments, a target level of G0F glycan within a range of 40% to 80% G0F relative to total glycan, where the method includes a selected level of galactose within a range of 15 mM to 30 mM and a time for cell culture that is within a range of 16 days to 60 days.

In some embodiments, provided methods further include measuring a level of G0F glycan. In some embodiments, if the measured level of G0F glycan is within a range of 20% to 80% G0F relative to total glycan (e.g., within a range of 20% up to 40% G0F relative to total glycan, e.g., within a range of 40% to 80% G0F relative to total glycan), then a step of purifying, concentrating, and/or formulating the ustekinumab preparation is performed.

In some embodiments, provided methods for manufacturing and/or producing ustekinumab having a target glycan level include a target level of sialylated glycan and/or G2F glycan. Provided in Table 1 below are conditions for ustekinumab with target levels of sialylated glycan and/or G2F glycan.

TABLE 1

Examplary Conditions for Production of Ustekinumab Preparations with Target G2F and Sialylated Glycan Levels

| Glycan Range | G2F | Total Sialylation |
| --- | --- | --- |
| NCM-1 (0 mM galactose, culture time 7-15 days) | >5%-10% | >15%-30% |
| NCM-2 (15-30 mM galactose, culture time 25-60 days) | 1%-5% | 5%-15% |

In some embodiments, provided methods are directed to manufacturing and/or producing ustekinumab having a target level of sialylated glycan within a range of 15% to 30% sialylated glycan relative to total glycan. In some embodiments, a method for achieving ustekinumab having a target level of sialylated glycan within a range of 15% to 30% sialylated glycan relative to total glycan includes a selected level of galactose at 0 mM and a time for cell culturing is within a range of 7 days to 15 days.

In some embodiments, provided methods are directed to manufacturing and/or producing ustekinumab having a target level of sialylated glycan within a range of 5% up to 15% sialylated glycan relative to total glycan. In some embodiments, a method for achieving ustekinumab having a target level of G0F glycan within a range of 5% up to 15% sialylated glycan relative to total glycan include a selected level of galactose within a range of 15 mM to 30 mM and a time for cell culture that is within a range of 16 days to 60 days. In some certain embodiments, a time for cell culturing is within a range of 25 days to 42 days.

In some embodiments, provided methods are directed to manufacturing and/or producing ustekinumab having a target level of G2F glycan within a range of 5% to 10% G2F relative to total glycan. In some embodiments, a method for achieving ustekinumab having a target level of G2F glycan within a range of 5% to 10% G2F relative to total glycan includes a selected level of galactose at 0 mM and a time for cell culture that is within a range of 7 days to 15 days.

In some embodiments, provided methods are directed to manufacturing and/or producing ustekinumab having a target level of G2F glycan within a range of 1% up to 5% G0F relative to total glycan. In some embodiments, a method for achieving ustekinumab having a target level of G2F glycan within a range of 1% up to 5% G2F relative to total glycan include a selected level of galactose within a range of 15 mM to 30 mM and a time for cell culture that is within a range of 16 days to 60 days. In some certain embodiments, a time for cell culturing is within a range of 25 days to 42 days.

In some embodiments, provided methods a selected level of galactose is controlled throughout the culturing step (e.g., controlled during culturing from t=0 until harvest).

In some embodiments, provided methods include culturing a population of mammalian cells that are genetically engineered to express ustekinumab. In some embodiments, mammalian cells are selected from: CHO cells, HEK 293 cells, fibrosarcoma HT 1080 cells, PER.C6 cells, CAP cells, HKB-11 cells, HuH-7 cells, NS0 cells and SP 2/0 cells.

In some embodiments, in the provided methods the culturing step is performed using continuous culture process. In some embodiments, provided methods include culturing that is performed using a perfusion culture process (e.g., an alternating tangential flow filter (ATF)-based perfusion culture process). In some certain embodiments, provided methods include culturing mammalian cells that are genetically engineered to express ustekinumab (e.g., SP 2/0 cells that express ustekinumab) by a perfusion culture process.

In some embodiments, provides methods including harvesting ustekinumab expressed by the cells at two or more times within the range of time of the time for cell culture.

In some embodiments, the target value is a predetermined pharmaceutical product specification or a quality control criterion for a pharmaceutical preparation, e.g., a Certificate of Analysis (CofA), a Certificate of Testing (CofT), or a Master Batch Record. In some embodiments, the product specification is a product description in an FDA label, a Physician's Insert, a USP monograph, or an EP monograph.

Generally, cell culture methods of the present disclosure including culturing at a temperature within a range of 25° C. to 40° C. and with gravity as it is encountered on earth. In some embodiments, provided methods of culturing a population of cells is sufficient for expression of an ustekinumab product. Cell culture media generally comprise an appropriate source of energy and compounds which regulate the cell cycle. Generally, culture media includes, for example amino acids, vitamins, inorganic salts, and glucose, which is known to those of skill in the art. In some embodiments, a cell culture media has a pH of 6 to 8. Media for animal cell culture are well established in the art, and are routinely optimized by the skilled artisan for the particular purpose and/or cell type.

In some embodiments, methods of the present disclosure include culturing a population of cells via a continuous cell culture system (e.g., perfusion cell culture system). In some embodiments, a continuous cell culture system includes bioreactor tank and a cell retention device. In some embodiments, a continuous cell culture system includes a bioreactor tank, a cell retention device, a media supply, and a bleed waste collection. In some embodiments, a continuous cell culture system includes a population of cells (e.g., a population of cells engineered to express ustekinumab, e.g., a population of cells consisting of cells engineered to express ustekinumab) and cell culture media.

In some embodiments, a cell retention device is or includes a continuous centrifuge, an alternating tangential flow filter (ATF), a tangential flow membrane filter (TFF), a dynamic filter, a spin-filter, an ultrasonic and dielectrophoretic separator, or a gravity settler. In some certain embodiments, a cell retention device is or includes an ATF.

In some embodiments, a bioreactor system includes a stirred-tank bioreactor, a cell retention device, a media supply, and a bleed waste collection.

In some embodiments, a bioreactor system (e.g., a perfusion bioreactor system) includes a sparger. In some embodiments, a bioreactor system includes a drilled hole sparger. In some embodiments, a bioreactor system includes an open pipe sparger. In some embodiments, a bioreactor system includes a sintered sparger.

In some embodiments, methods of the present disclosure include culturing a population of cells (e.g., a population of cells engineered to express ustekinumab, e.g., a population of cells consisting of cells engineered to express ustekinumab) at a volume within a range of 1 L to 3000 L. In some embodiments, provided methods include culturing mammalian cells that are genetically engineered to express ustekinumab at a volume of at least 25 L, 50 L, 100 L, 200 L, 250 L, 400 L, 500 L, 600 L, 800 L, 1000 L, or 2000 L. In some embodiments, provided methods include culturing mammalian cells that are genetically engineered to express ustekinumab at a volume of about 25 L to about 250 L.

Glycan Evaluation

In some embodiments, glycans of ustekinumab are analyzed (e.g., measured) by any available suitable method. In some instances, glycan structure and composition as described herein are analyzed, for example, by one or more, enzymatic, chromatographic, mass spectrometry (MS), chromatographic followed by MS, electrophoretic methods, electrophoretic methods followed by MS, nuclear magnetic resonance (NMR) methods, and combinations thereof. Exemplary enzymatic methods include contacting a ustekinumab preparation with one or more enzymes under conditions and for a time sufficient to release one or more glycan(s) (e.g., one or more exposed glycan(s)). In some instances, the one or more enzymes include(s) PNGase F. Exemplary chromatographic methods include, but are not limited to, Strong Anion Exchange chromatography using Pulsed Amperometric Detection (SAX-PAD), liquid chromatography (LC), high performance liquid chromatography (HPLC), ultra-performance liquid chromatography (UPLC), thin layer chromatography (TLC), amide column chromatography, and combinations thereof. Exemplary mass spectrometry (MS) include, but are not limited to, tandem MS, LC-MS, LC-MS/MS, matrix assisted laser desorption ionization mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof. Exemplary nuclear magnetic resonance (NMR) include, but are not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

Cells

Any host cell that can be used to express ustekinumab can be used in the methods described herein. In some embodiments, a cell engineered to express ustekinumab includes one or more nucleic acids that encode an ustekinumab product that includes a heavy chain variable domain as set forth in SEQ ID NO.: 1 and/or a light chain variable domain as set forth in SEQ ID NO.: 2. In some embodiments, a cell engineered to express ustekinumab includes one or more nucleic acids that encode an ustekinumab product that includes a heavy chain comprising a sequence of SEQ ID NO.: 1 and/or a light chain comprising a sequence of SEQ ID NO.: 2. In some embodiments, a cell engineered to express ustekinumab includes one or more nucleic acids that encode an ustekinumab product that includes HCDR1, HCDR2, and HCDR3 sequences as set forth in SEQ ID NO.: 1 and LCDR1, LCDR2, and LCDR3 sequences as set forth in SEQ ID NO.: 2.

In some embodiments, a cell engineered to express ustekinumab includes one or more nucleic acids that encode an ustekinumab product that has the same primary amino acid sequence as a protein that has been approved, e.g., under a secondary approval process, for therapeutic or diagnostic use in humans or animals. In some embodiments, a cell engineered to express ustekinumab includes one or more nucleic acids that encode an ustekinumab product that differs by no more than 1, 2, 3, 4, 5, 6, 7, 8, 9, 10, 15, or 20 residues with an approved therapeutic or diagnostic protein. In some embodiments, a cell engineered to express ustekinumab includes one or more nucleic acids that encode a protein that has at least 90, 95, 98, 99% or 100% sequence identity with that of an approved therapeutic or diagnostic protein. The terms the "same primary amino acid sequence", "a primary amino acid sequence that differs by no more than 1, 2, 3, 4, 5, 6, 7, 8, 9, 10, 15, or 20 residues", "sequences that have at least 98% or more sequence identity", or similar terms, relate to level of identity between primary amino acid sequences. In some embodiments, a protein preparation or product includes amino acid variants, e.g., species that differ at terminal residues, e.g., at one or two terminal residues. In some embodiments of such cases, sequence identity compared is the identity between the primary amino acid sequence of the most abundant (e.g., most abundant active) species in each of the products being compared. In some embodiments, sequence identity refers to the amino acid sequence encoded by a nucleic acid that can be used to make the ustekinumab product.

In some embodiments, cells engineered to express ustekinumab are mammalian cells.

In some embodiments, cells engineered to express ustekinumab are murine cells. In some embodiments, a cell engineered to express ustekinumab is from a mouse cell line. Murine (e.g., mouse) cell lines include, for example, mouse myeloma cell lines, e.g., NS0 cells and SP 2/0 cells.

In some embodiments, cells engineered to express ustekinumab are human cells. In some embodiments, a cell engineered to express ustekinumab is from a human cell line. Human cell lines include, for example, HEK 293: human embryonic kidney 293; HT-1080: from a fibrosarcoma with an epithelial-like phenotype; PER. C6: from human embryonic retinal cells immortalized via transfection with the adenovirus E1 gene; CAP: from human amniocytes immortalized through an adenovirus type 5 E1 gene; HKB-11: created through polyethylene glycol fusion of HEK293-S and a human B-cell line; and HuH-7: from a human hepatocellular carcinoma. In some certain embodiments, shear-sensitive cells are selected from: HEK 293 cells, fibrosarcoma HT 1080 cells, PER.C6 cells, CAP cells, HKB-11 cells and HuH-7 cells.

In some embodiments, a population of cells that express an ustekinumab product as described herein is produced using recombinant methods. Recombinant expression of a gene, such as a gene encoding a polypeptide, such as an antibody agent described herein, can include construction of an expression vector containing a polynucleotide that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

Once an ustekinumab product described herein has been produced by recombinant expression, it can be purified by any method known in the art for purification, for example, by chromatography (e.g., ion exchange, affinity, and sizing column chromatography), centrifugation, differential solubility, or by any other standard technique for the purification of proteins. For example, ustekinumab can be isolated and purified by appropriately selecting and combining affinity columns such as Protein A column with chromatography columns, filtration, ultra-filtration, salting-out and dialysis procedures (see Antibodies: A Laboratory Manual, Ed Harlow, David Lane, Cold Spring Harbor Laboratory, 1988). Further, as described herein, an ustekinumab product can be fused to heterologous polypeptide sequences to facilitate purification.

Pharmaceutical Compositions

A ustekinumab product produced or manufactured using any of the methods, systems and/or processes described herein can be incorporated into a pharmaceutical composition. Such a pharmaceutical composition may be useful in the prevention and/or treatment of diseases. Pharmaceutical compositions comprising ustekinumab can be formulated by methods known to those skilled in the art (see, e.g., Remington's Pharmaceutical Sciences, 20th Ed., Lippincott Williams & Wilkins, 2000). The pharmaceutical composition can be administered parenterally in the form of an injectable formulation comprising a sterile solution or suspension in water or another pharmaceutically acceptable liquid. For example, the pharmaceutical composition can be formulated by suitably combining the cell product (e.g., a recombinant protein, e.g., a glycoprotein, e.g., an antibody agent) with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in a pharmaceutical preparation is such that a suitable dose within the designated range is provided.

In some embodiments, a preparation of ustekinumab includes sucrose as a stabilizer/tonicifier. In some embodiments, a preparation of ustekinumab includes histidine (e.g., L-histidine) as a buffer. In some embodiments, a preparation of ustekinumab includes polisorbate 80 as a surfactant. In some certain embodiments, a preparation of ustekinumab includes histidine (e.g., L-histidine), sucrose, and polisorbate 80.

In some embodiments, a preparation of ustekinumab is formulated for parenteral administration, e.g., intravenous injection, intramuscular injection, intraperitoneal injection, subcutaneous injection. In some embodiments, a preparation of ustekinumab is formulated for subcutaneous administration.

The disclosure is further illustrated by the following examples. The examples are provided for illustrative purposes only. They are not to be construed as limiting the scope or content of the disclosure in any way.

EXAMPLES

Example 1: Identification of Shift in Glycan Composition of Ustekinumab Products This example identifies a significant shift in glycan composition among lots of commercially available ustekinumab reference protein products ("RPPs"). Specifically, the present example demonstrates that the variability in the glycan composition among lots of commercially available ustekinumab that segregates into two distinct glycan profiles. These two groups of glycan variants are referred to herein as "Group 1," which are characterized by a relatively high level of G0F glycan, and "Group 2," which characterized by a relatively low level of G0F glycan.

Thirty (30) lots of ustekinumab RPPs were analyzed. Among these 30 lots, 28 lots were from 90 mg/mL preparations and 2 lots were 5 mg/mL preparations. Of the 28 lots of 90 mg/mL ustekinumab RPPs, eight (8) of these lots were identified as having a Group 1 glycan profile and twenty (20) lots were identified as having a Group 2 glycan profile. See, FIG. 1.

A summary of the average abundance of each of the major glycan species for Group 1 and Group 2 samples is summarized in Table 2 below.

TABLE 2

Abundance of Major Glycans in Group 1 and Group 2 Ustekinumab Samples

| Glycan (%) | Group 1 | Group 2 |
|---|---|---|
| 4, 3, 1, 0, 0 (G0F) | 27.7 | 62.1 |
| 4, 4, 1, 0, 0 A (G1F-A) | 28.1 | 14.1 |
| 4, 4, 1, 0, 0 B (G1F-B) | 6.6 | 3.5 |
| 4, 4, 1, 0, 1 A | 5.4 | 4.1 |
| 4, 4, 1, 0, 1 B | 3.2 | 2.9 |
| 4, 5, 1, 0, 0 (G2F) | 8.4 | 2.3 |
| 4, 6, 1, 0, 0 | 1.4 | 0.2 |
| 4, 5, 1, 0, 1 | 6.7 | 2.1 |
| 4, 5, 1 ,0, 2 | 2.0 | 0.9 |
| 4, 6, 1, 0, 1 B | 3.4 | 0.7 |
| Sum of above | 92.9 | 92.9 |

Ustekinumab test products generated by culturing (e.g., by an ATF-based perfusion culture process) with 5 mM galactose for a duration of 42 days at different volumes within a range of 3 L to 250 L were also analyzed. The glycan abundance of these ustekinumab test products is depicted in the right most grouping of each panel of FIG. 1.

Figure 1:
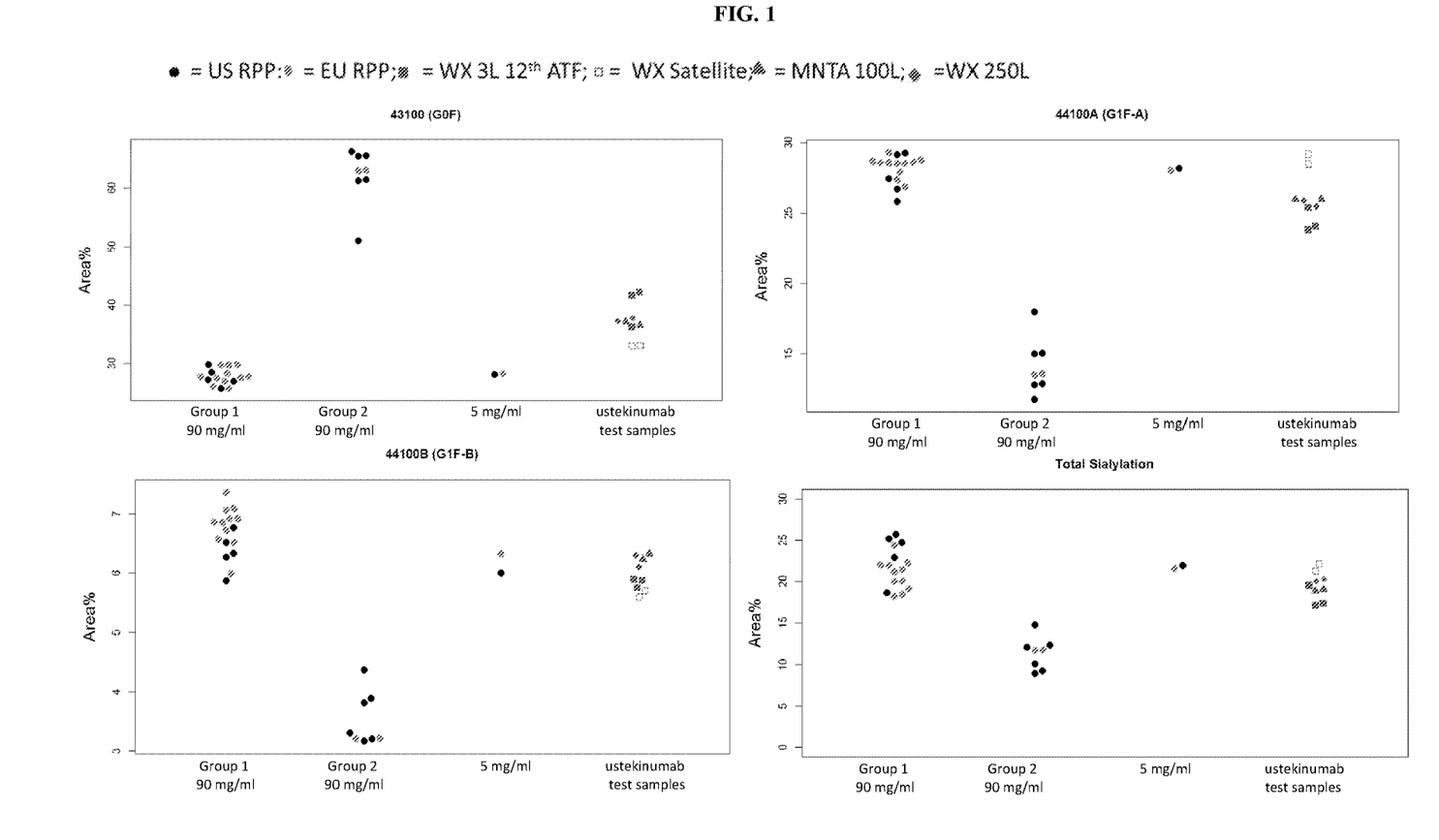

The glycan profiles of the ustekinumab test products were within the range of those of Group 1 and Group 2 RPPs. Thus, the present example identified two distinct groups of glycan profiles for commercially available ustekinumab RPPs and demonstrated that contemporaneous culture conditions yield ustekinumab test products with intermediate glycan abundances within the ranges of these two groups.

Example 2: Culture Time Affects Ustekinumab Glycan Composition

Figure 2:
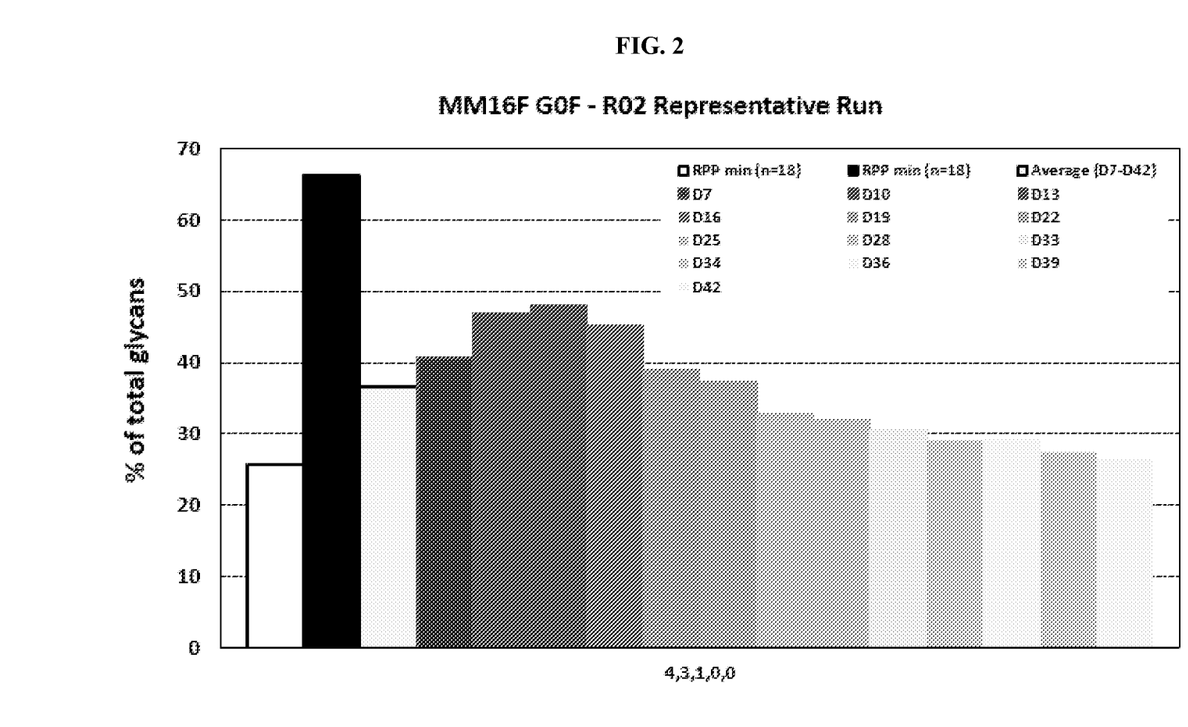
FIG. 2 depicts G0F glycan profile variation with harvest duration. Left-most column (white) represents Group 1 RPP G0F abundance, second column from the left (black) represents Group 2 RPP G0F abundance, third column from the left represents the average abundance of G0F from samples cultured between 7 days and 42 days. Shaded columns (starting at fourth column from the left and continuing to the right most column) each represent the G0F abundance from samples cultured an indicated number of days within a range of 7 days (D7) up to 42 days (D42, right most column).

The present example demonstrates that harvest collection timing is an element for controlling ustekinumab glycan composition. As depicted in FIG. 2 the abundance of G0F glycan relative to total glycan generally decreased with culture duration. For example, ustekinumab preparations that were harvested at 13 days of culturing had an almost 50% abundance of G0F glycans, while samples with harvested after 34 or more days of culturing had less than 30% G0F glycans relative to total glycan composition.

Interesting, the present disclosure provides the recognition that a decrease in the culture duration (i.e. time till harvest) is coupled with an increase in G0F level; while an increase in the culture duration (i.e. time till harvest) is coupled with a reduction in G0F level.

Thus, this example demonstrates that increasing culture time can decrease abundance of G0F glycans relative to total glycan composition and further describes that culture time can be varied to control ustekinumab glycan composition.

Example 3: Generation of Ustekinumab Products with Group 1 and Group 2 Glycan Profiles The present example identifies an inverse relationship between culture time and galactose concentration in culture media that can serve as a process lever for controlling ustekinumab glycan levels (e.g., galactosylation). The present example demonstrates production of non-conforming materials (i.e., non-conforming ustekinumab preparations) with engineered glycan profiles. Specifically, the present example demonstrate production of two non-conforming ustekinumab preparations, referred to herein as NCM-1 and NCM-2, that have been engineered to have glycan profiles that match that of Group 1 RPP and Group 2 RPP, respectively, as described above in Example 1.

Figure 3A:
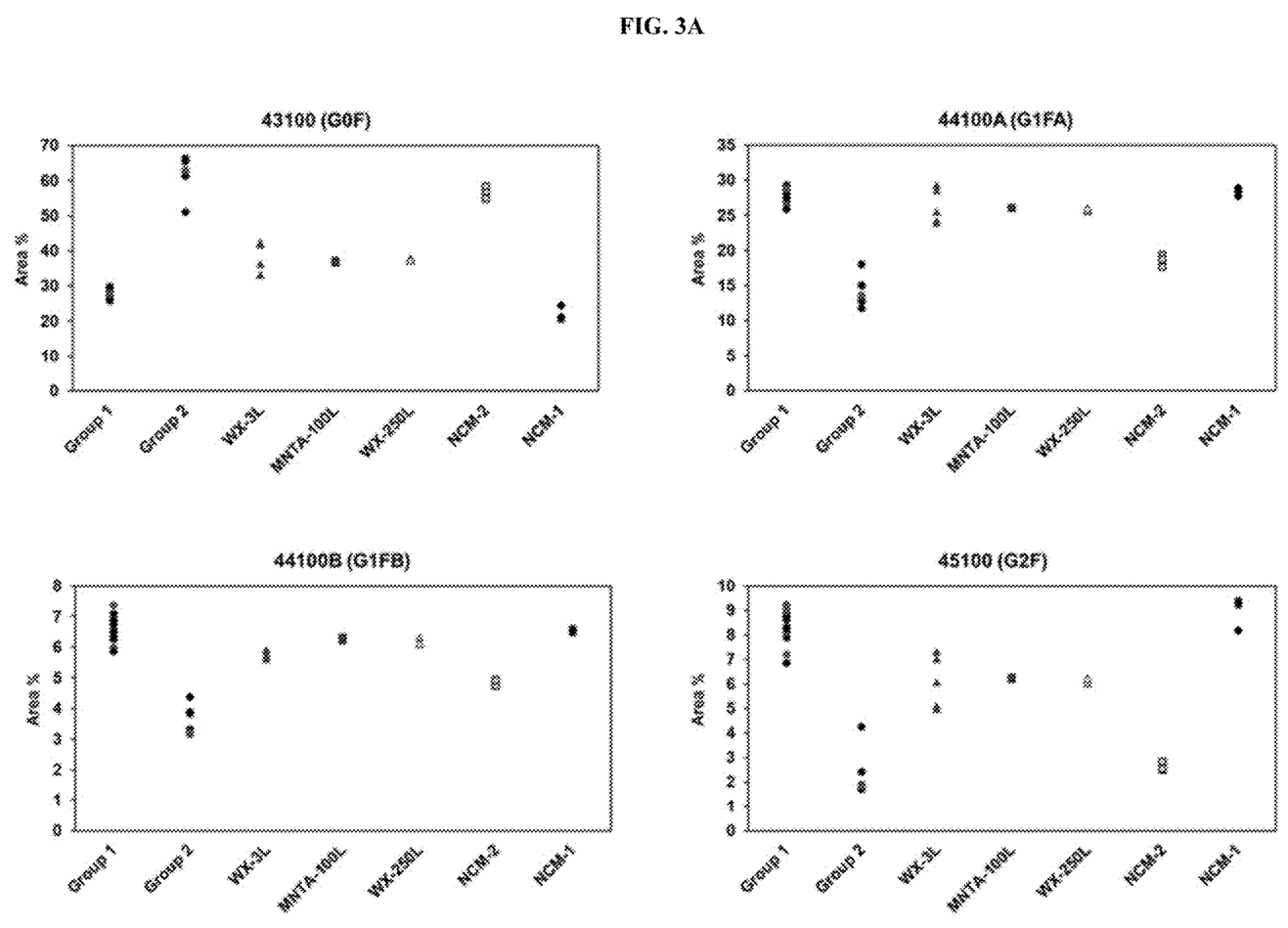
FIG. 3A shows G1FA, G2F, G0F, and G1FB glycan profiles.
Figure 3B:
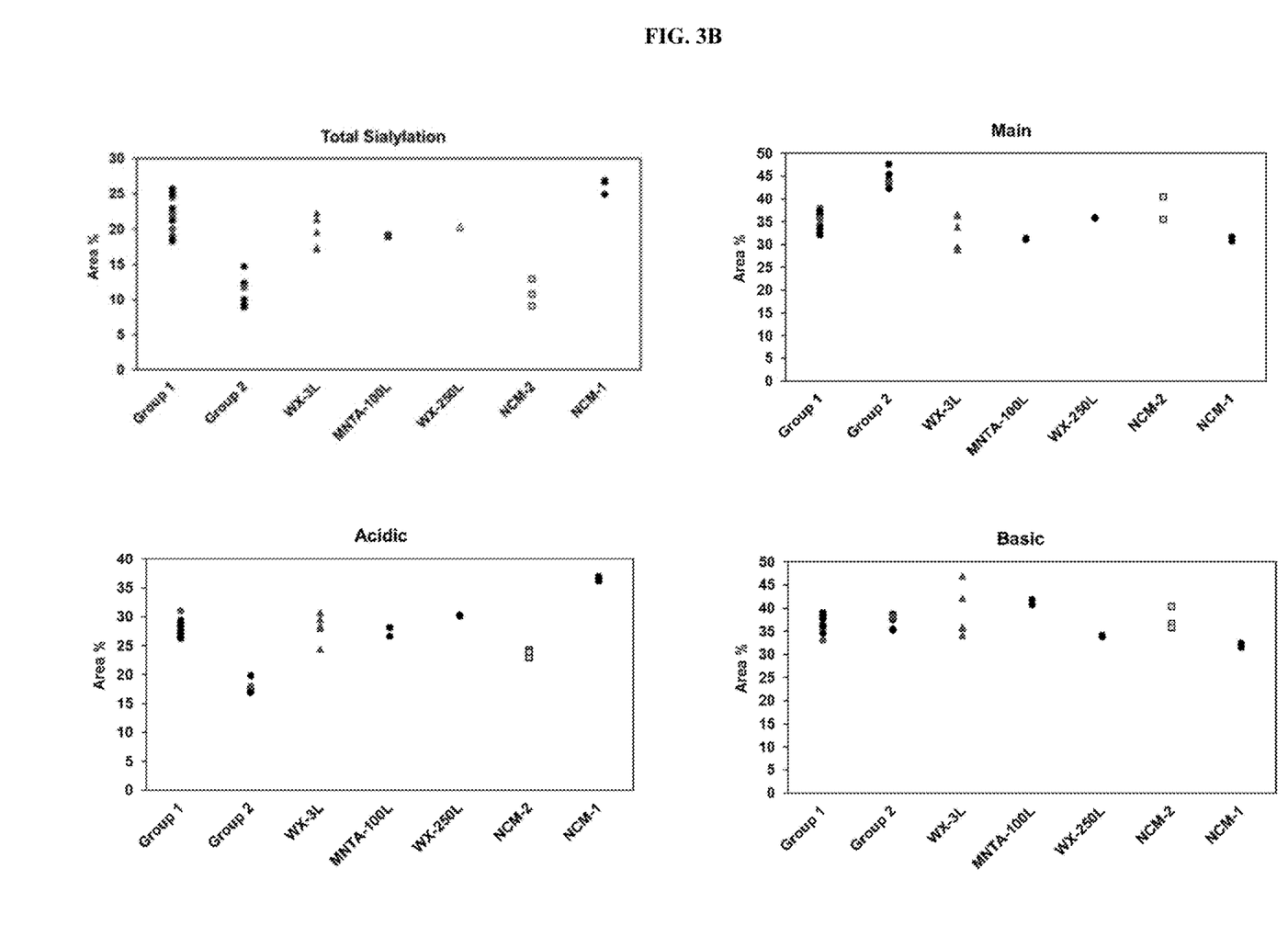
FIG. 3B shows main, basic, total sialylation, and acidic glycan profiles.

Specifically, NCM-1 preparations were generated by culturing (e.g., by an ATF-based perfusion culture process) with 15 mM galactose and harvesting ustekinumab before day 16 of culturing (e.g., harvesting at time points within a range of day 7 to day 15). In contrast, NCM-2 preparations were generated by culturing (e.g., by an ATF-based perfusion culture process) in a medium lacking galactose (0 mM galactose) and harvesting ustekinumab after day 25 of culturing (e.g., harvesting at time points within a range of day 34 to day 45). As depicted in FIGS. 3A-3B, NCM-1 glycan profiles correlated well with those of Group 1 RPP and NCM-2 glycan profiles correlated well with those of Group 2 RPP for each of the glycan species analyzed, including G0F, G1FA, G1FB, G2F, total sialyation, main, acidic and basic glycans. Table 3 provides exemplary target ranges for each glycan as engineered by controlling the process levers of galactose concentration and culture time.

TABLE 3

Exemplary Target Glycan Ranges of NCM-1 and NCM-2 Ustekinumab Preparations

| Glycan Range | G0F | G1F-A | G1F-B | G2F | Total Sialylation |
|---|---|---|---|---|---|
| NCM-1 (0 mM galactose, culture time 7-15 days) | 20%-40% | >25%-35% | >5.5%-10% | >5%-10% | >15%-30% |
| NCM-2 (15-30 mM galactose, culture time 25-60 days) | >40%-80% | 10%-25% | 2%-5.5% | 1%-5% | 5%-15% |

Thus, the present example demonstrated that inversely related elements of galactose concentration and culture time can be used as process levers to control glycan composition and can be used to produce non-conforming ustekinumab preparations with target glycan levels.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method of manufacturing a pharmaceutical composition comprising ustekinumab having a target level of G0F glycan, the method comprising:
   (a) selecting a target level of G0F glycan, wherein the target level of G0F glycan is within a range of 20% to 80% G0F relative to total glycan;
   (b) selecting a level of galactose and a time for cell culture to provide the selected level of G0F glycan, wherein the level of galactose is within a range of 0 mM to 30 mM; and
   the time for cell culture is within a range of 7 to 60 days;
   (c) culturing a population of cells genetically engineered to express ustekinumab under conditions comprising the selected level of galactose and time;
   (d) harvesting ustekinumab expressed by the population of cells, thereby producing the preparation of ustekinumab; and
   (e) purifying, concentrating, and/or formulating the ustekinumab preparation to produce the pharmaceutical composition comprising ustekinumab if the preparation meets the target level of G0F glycan.

2. The method of claim 1, wherein the culturing is performed using a perfusion culture process.

3. The method of claim 1, wherein the target level of G0F glycan is within a range of 25% to 65% G0F relative to total glycan.

4. The method of claim 1, wherein the target level of G0F glycan is within a range of 20% up to 40% G0F relative to total glycan, wherein the selected level of galactose is 0 mM, and wherein the time for cell culture is within a range of 7 days to 15 days.

5. The method of claim 1, wherein the target level of G0F glycan is within a range of 40% to 80% G0F relative to total glycan, wherein the selected level of galactose is within a range of 15 mM to 30 mM, and wherein the time for cell culture is within a range of 16 days to 60 days.

6. The method of claim 5, wherein the time for cell culture is within a range of 25 days to 42 days.

7. The method of claim 5, wherein the time for cell culture is within a range of 25 days to 60 days.

8. The method of claim 1, further comprising measuring a level of G0F glycan.

9. The method of claim 1, wherein the population of cells genetically engineered to express ustekinumab are mammalian cells.

10. The method of claim 9, wherein the mammalian cells are selected from CHO cells, HEK1 293 cells, fibrosarcoma HT 1080 cells, retinal cells, amniocyte cells, HKB-11 cells, HuH-7 cells, NS0 cells and SP 2/0 cells.

11. The method of claim 1, wherein the selected level of galactose is controlled during culturing from t=0 until harvest.

12. The method of claim 1, wherein the ustekinumab expressed by the cells is harvested two or more times within the time range of the time for cell culture.

13. The method of claim 1, wherein the level of galactose is 0 mM.

14. The method of claim 1, wherein the level of galactose is 15 mM to 30 mM.

15. The method of claim 1, wherein the time for cell culture is within a range of 7 days to 15 days.

16. The method of claim 1, wherein the time for cell culture is within a range of 16 days to 60 days.

* * * * *